US012623086B2

(12) United States Patent　　　　　(10) Patent No.:　US 12,623,086 B2
DeBardi et al.　　　　　　　　　　　　(45) **Date of Patent:　*May 12, 2026**

(54) SYSTEM FOR MULTIPLE DEFIBRILLATION THERAPIES

(71) Applicant: Physio-Control, Inc., Redmond, WA (US)

(72) Inventors: Gary DeBardi, Kirkland, WA (US); Fred W. Chapman, Newcastle, WA (US); Tyson G. Taylor, Bothell, WA (US); Ronald E. Stickney, Edmonds, WA (US)

(73) Assignee: Physio-Control, Inc., Redmond, WA (US)

( * ) Notice: Subject to any disclaimer, the term of this patent is extended or adjusted under 35 U.S.C. 154(b) by 498 days.

This patent is subject to a terminal disclaimer.

(21) Appl. No.: 18/128,210

(22) Filed: Mar. 29, 2023

(65) Prior Publication Data

US 2023/0293898 A1　　Sep. 21, 2023

Related U.S. Application Data

(63) Continuation of application No. 16/833,259, filed on Mar. 27, 2020, now Pat. No. 11,642,541, which is a continuation of application No. 15/788,704, filed on Oct. 19, 2017, now Pat. No. 10,632,320.

(60) Provisional application No. 62/410,290, filed on Oct. 19, 2016.

(51) Int. Cl.
　*A61N 1/39*　　　(2006.01)
　*A61B 5/25*　　　(2021.01)
　*A61N 1/04*　　　(2006.01)

(52) U.S. Cl.
　CPC .............. *A61N 1/3987* (2013.01); *A61B 5/25* (2021.01); *A61N 1/046* (2013.01); *A61N 1/3937* (2013.01)

(58) Field of Classification Search
　CPC .... A61N 1/046; A61N 1/3937; A61N 1/3987; A61B 5/25
　See application file for complete search history.

(56) References Cited

U.S. PATENT DOCUMENTS

| | | | |
|---|---|---|---|
| 5,215,083 | A | 6/1993 | Drane et al. |
| 6,327,500 | B1 | 12/2001 | Cooper et al. |
| 6,711,442 | B1 | 3/2004 | Swerdlow et al. |
| 2005/0209647 | A1 | 9/2005 | Wanasek et al. |
| 2007/0299473 | A1 | 12/2007 | Matos |

(Continued)

OTHER PUBLICATIONS

Erich, J., "Hold the Coroner," EMSWorld, published Apr. 30, 2011, retrieved from <<http://www.emsworld.com/article/10318805/hold-coroner>>, on Oct. 19, 2017, 3 pages.

(Continued)

*Primary Examiner* — Christopher A Flory
(74) *Attorney, Agent, or Firm* — Lee & Hayes, P.C.

(57)　　　　ABSTRACT

A defibrillation system for the administration of a dual sequential defibrillation and/or simultaneous defibrillation therapy. A first defibrillation device is inductively coupled to a second defibrillation device. An energy delivery of the first defibrillation device generating, or causing to be generated, an artifact that is received by the second defibrillation device. The artifact causing a sync mode, or sync mode circuitry, of the second defibrillation device to administer a second energy delivery. The second energy delivery can be delayed relative to the energy delivery by the first defibrillation device.

19 Claims, 9 Drawing Sheets

MULTI-DEFIBRILLATION SYSTEM

(56)  References Cited

U.S. PATENT DOCUMENTS

| | | | |
|---|---|---|---|
| 2008/0004663 A1 | 1/2008 | Jorgenson |
| 2009/0054940 A1 | 2/2009 | Jorgenson |
| 2010/0317942 A1 | 12/2010 | Cinbis et al. |
| 2014/0005735 A1 | 1/2014 | Jorgenson |
| 2014/0194940 A1 | 7/2014 | De Bellis |
| 2015/0367138 A1 | 12/2015 | Gilman et al. |
| 2016/0121132 A1 | 5/2016 | Herleikson |
| 2018/0169426 A1 | 6/2018 | Montague et al. |
| 2018/0280709 A1 | 10/2018 | Taylor et al. |

OTHER PUBLICATIONS

Johnson, et al., "Effect of Pulse Separation Between Two Sequential Biphasic Shocks Given Over Different Lead Configurations on Ventricular Defibrillation Efficacy," Circulation, American Heart Association, vol. 85, No. 6, Jun. 1992, pp. 2267-2274.

Office Action for U.S. Appl. No. 16/833,259, mailed on Oct. 21, 2022, DeBardi, "System for Multiple Defibrillation Therapies", 6 pages.

Office Action for U.S. Appl. No. 15/788,704, mailed on Aug. 29, 2019, DeBardi, "System for Multiple Defibrillation Therapies," 11 pages.

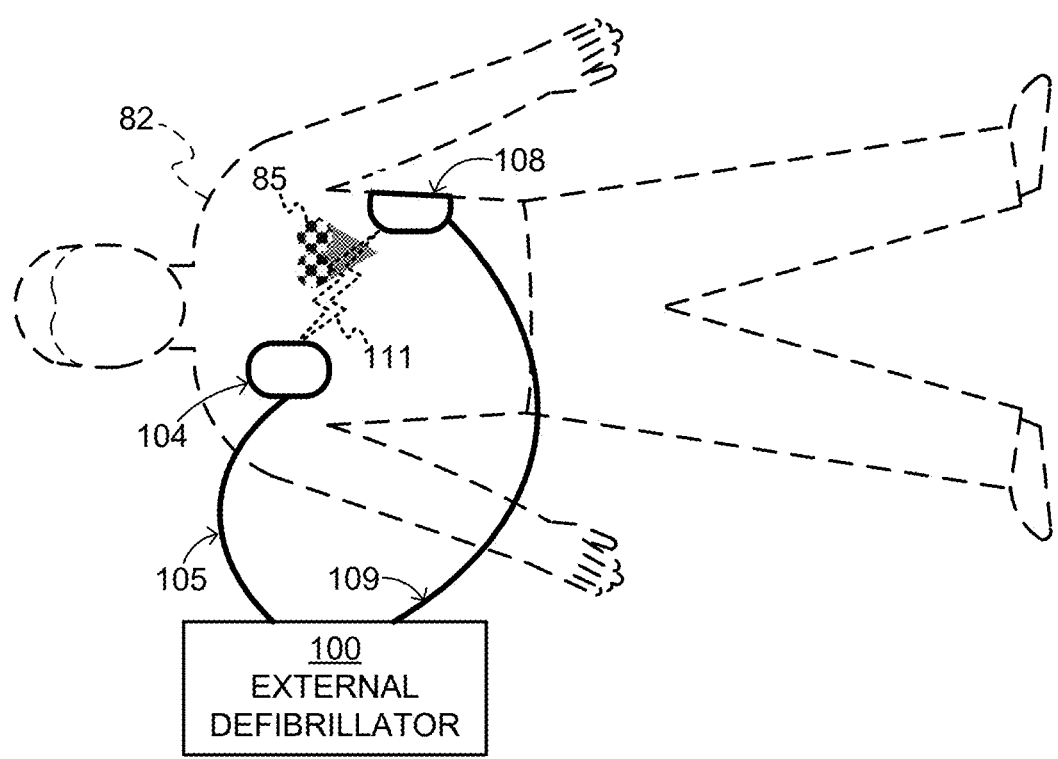
FIG. 1          *DEFIBRILLATION SCENE*
| TYPE OF EXTERNAL DEFIBRILLATOR | INTENDED TO BE USED BY PERSONS: | |
|---|---|---|
| | IN THE MEDICAL PROFESSIONS | NOT IN THE MEDICAL PROFESSIONS |
| DEFIBRILLATOR – MONITOR | √ | |
| AED | √ | √ |
FIG. 2          *TWO MAIN TYPES OF EXTERNAL DEFIBRILLATORS*

COMPONENTS OF EXTERNAL DEFIBRILLATOR

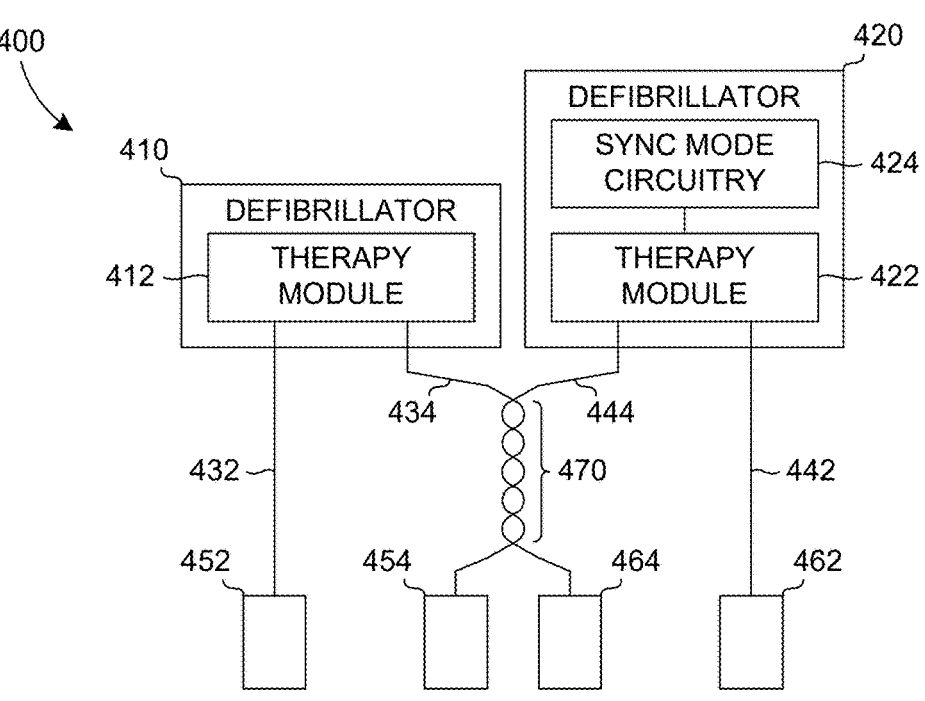
FIG. 4 _MULTI-DEFIBRILLATION SYSTEM_
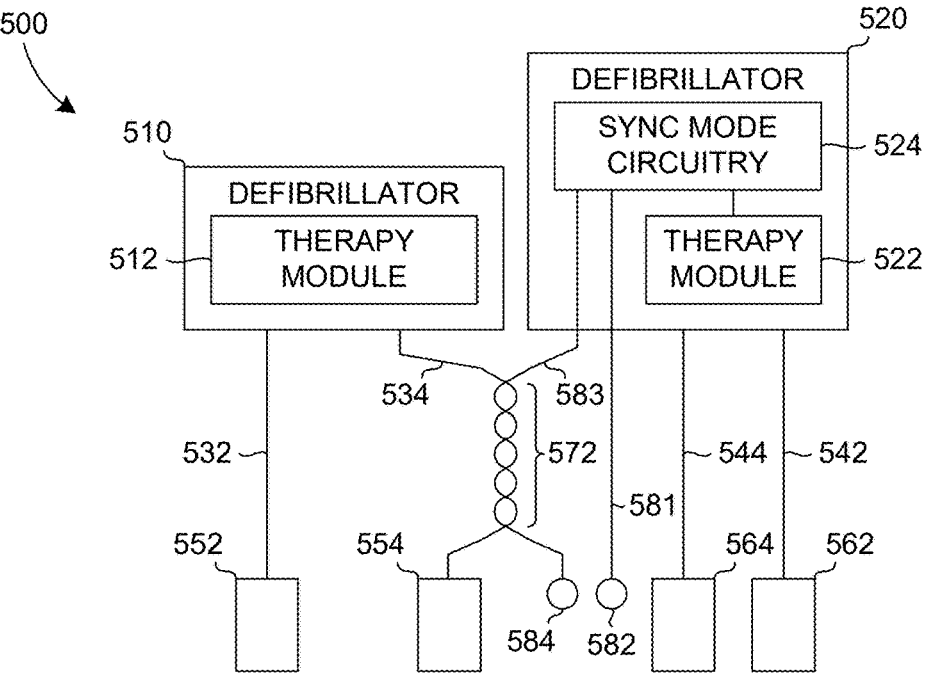
FIG. 5 _MULTI-DEFIBRILLATION SYSTEM_

600
610
620
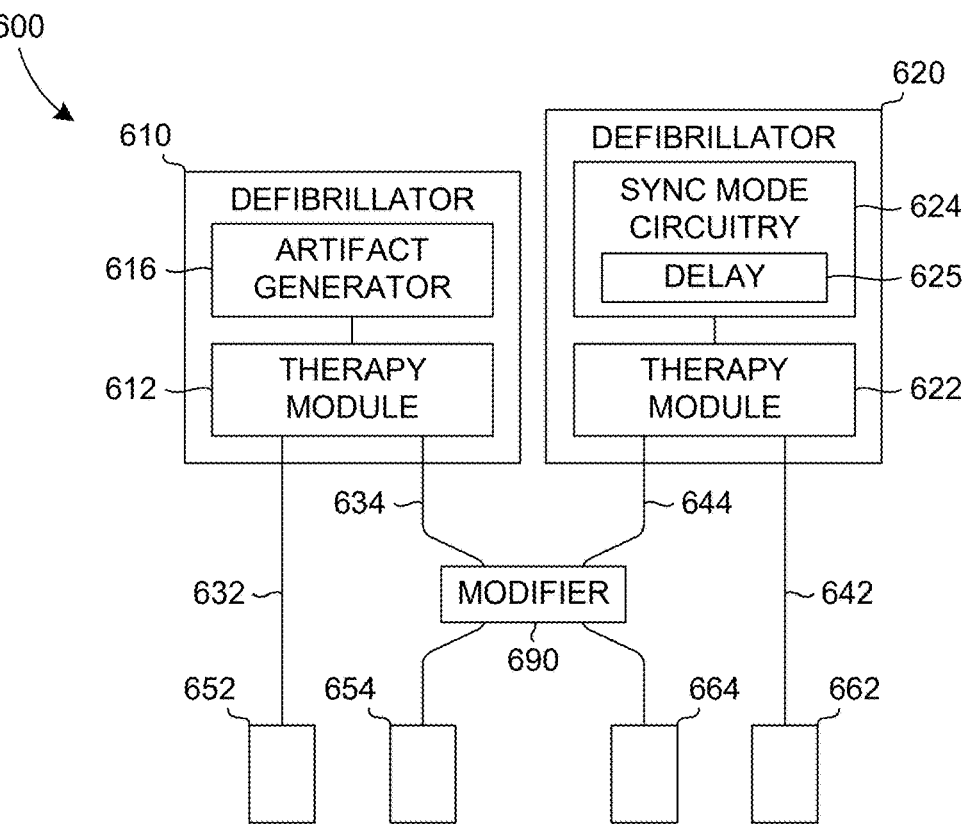
616
DEFIBRILLATOR
ARTIFACT
GENERATOR
612
THERAPY
MODULE
DEFIBRILLATOR
SYNC MODE
CIRCUITRY    624
DELAY    625
THERAPY
MODULE    622
634    644
632    MODIFIER    642
690
652    654    664    662
FIG. 6    *MULTI-DEFIBRILLATION SYSTEM*
700
720    730
710
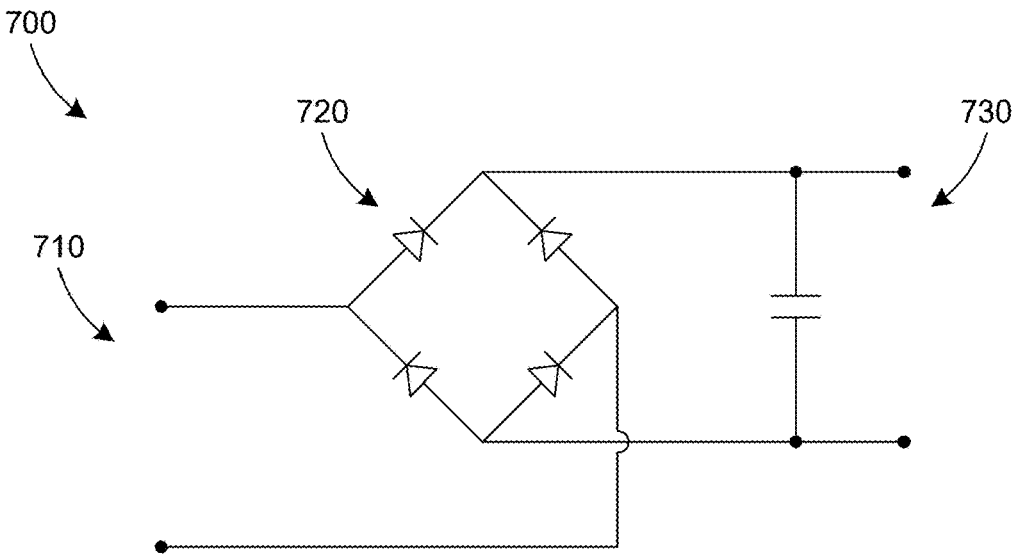
FIG. 7    *PASSIVE MODIFIER CIRCUIT DIAGRAM*

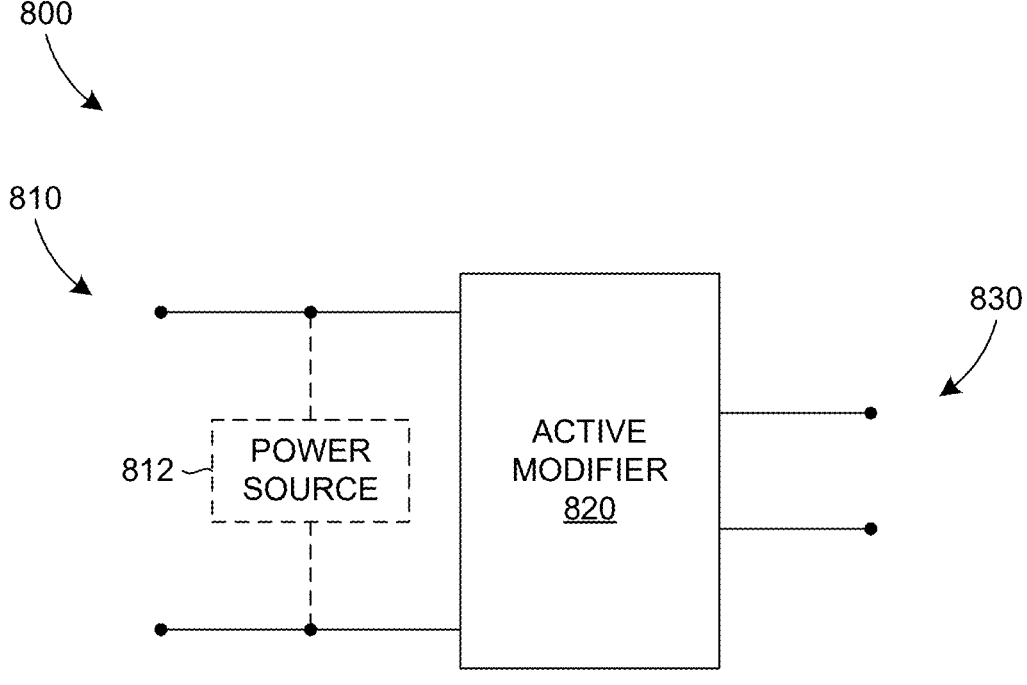
800
810
830
812
POWER
SOURCE
ACTIVE
MODIFIER
820
FIG. 8     _ACTIVE MODIFIER CIRCUIT DIAGRAM_

*ADMINISTRATION OF MULTIPLE DEFIBRILLATION THERAPIES*

ADMINISTRATION OF MULTIPLE DEFIBRILLATION THERAPIES IN RESPONSE TO ATRIAL FIBRILLATION

1100

DEVICE FOR INTERTWINING WIRES

1200
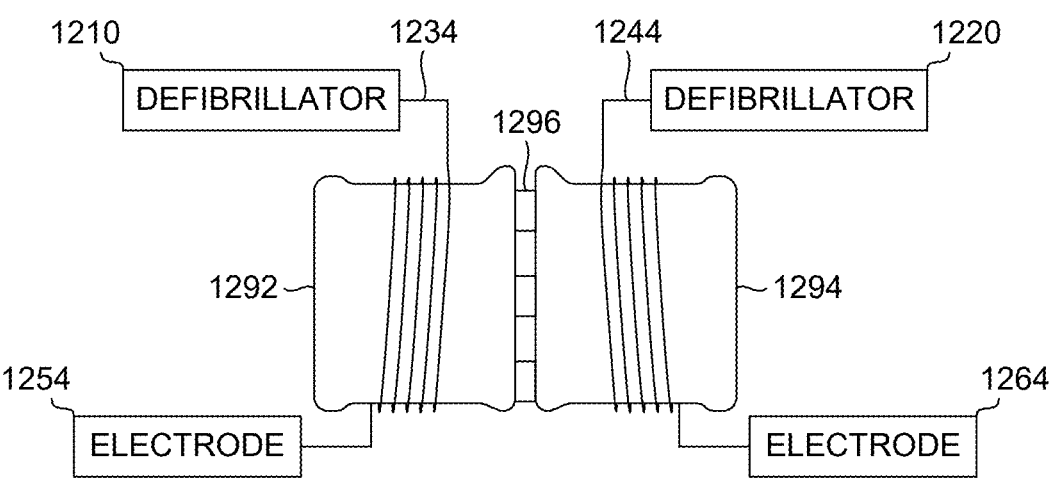
FIG. 12
*DEVICE FOR INTERTWINING WIRES*
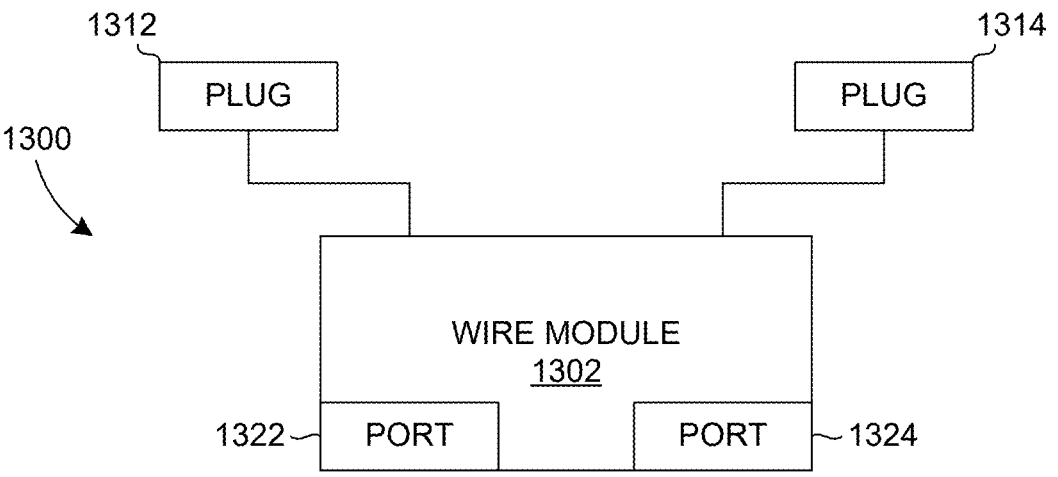
FIG. 13
*DEVICE WITH INTERTWINED WIRES*

SYSTEM FOR MULTIPLE DEFIBRILLATION THERAPIES

CROSS-REFERENCE TO RELATED APPLICATIONS

This application is a continuation of U.S. application Ser. No. 16/833,259, filed Mar. 27, 2020, which is a continuation of U.S. application Ser. No. 15/788,704, filed Oct. 19, 2017, which claims the benefit of U.S. Provisional Patent Application Ser. No. 62/410,290, filed on Oct. 19, 2016, the contents of each of which are herein incorporated by reference in their entirety.

BACKGROUND

Double sequential defibrillation (DSD) or simultaneous/near simultaneous defibrillation is a treatment protocol that is growing in use and popularity to treat patients suffering from cardiac arrest. For a patient in ventricular fibrillation, and especially for a patient suffering from refractory ventricular fibrillation, the use of DSD or simultaneous defibrillation may be an effective treatment in helping restore the patient's normal heart rhythm. Conventionally, DSD has been performed as a last ditch effort to try and save the life of a patient suffering a difficult-to-terminate cardiac arrhythmia. The administration of DSD has been haphazard, poorly timed, and uncoordinated. Typically, DSD or simultaneous defibrillation is administered using two separate and distinct defibrillators, such as two monitor/defibrillators (sometimes referred to as manual defibrillators), or two automated external defibrillators (AEDs), or a monitor/defibrillator and an AED. Human rescuers manually time the two (or more) defibrillation shocks to be delivered to the patient at the correct time but the time precision with which the shocks must be delivered for effective treatment is likely greater that what can be achieved manually.

Relying on human ability and/or judgement to administer shocks from two separate defibrillators in a coordinated manner is an imperfect system that results in questionable therapy outcomes due to improper shock delivery timing. Improper timing of the shock delivery can potentially lengthen the amount of time a patient experiences cardiac arrest with ventricular fibrillation or can potentially cause fatal additional arrhythmias to the patient's heart (for example, inducing ventricular fibrillation while attempting to treat atrial fibrillation).

DSD and simultaneous defibrillation is becoming more widely adopted for patients suffering from cardiac arrest. The art would benefit from systems and/or methods for assisting in proper delivery of such therapies with precise timing control and reproducible timing of multiple shock deliveries.

BRIEF DESCRIPTION OF THE DRAWINGS

FIG. 1 is a diagram of a scene where an external defibrillator is used to save the life of a person according to embodiments.

FIG. 2 is a table listing two main types of the external defibrillator shown in FIG. 1, and who they might be used by.

FIG. 4 is an example system for delivering multiple defibrillation therapies.

FIG. 5 is a further example system for delivering multiple defibrillation therapies.

FIG. 6 is yet another example system for delivering multiple defibrillation therapies.

FIG. 7 is an example circuit diagram of a modifier for use with a system for delivering multiple defibrillation therapies.

FIG. 8 is another example circuit diagram of a modifier for use with a system for delivering multiple defibrillation therapies.

FIG. 12 is another example of hardware for intertwining wires.

FIG. 13 is yet another example hardware for intertwined wires.

SUMMARY

Figure 3:
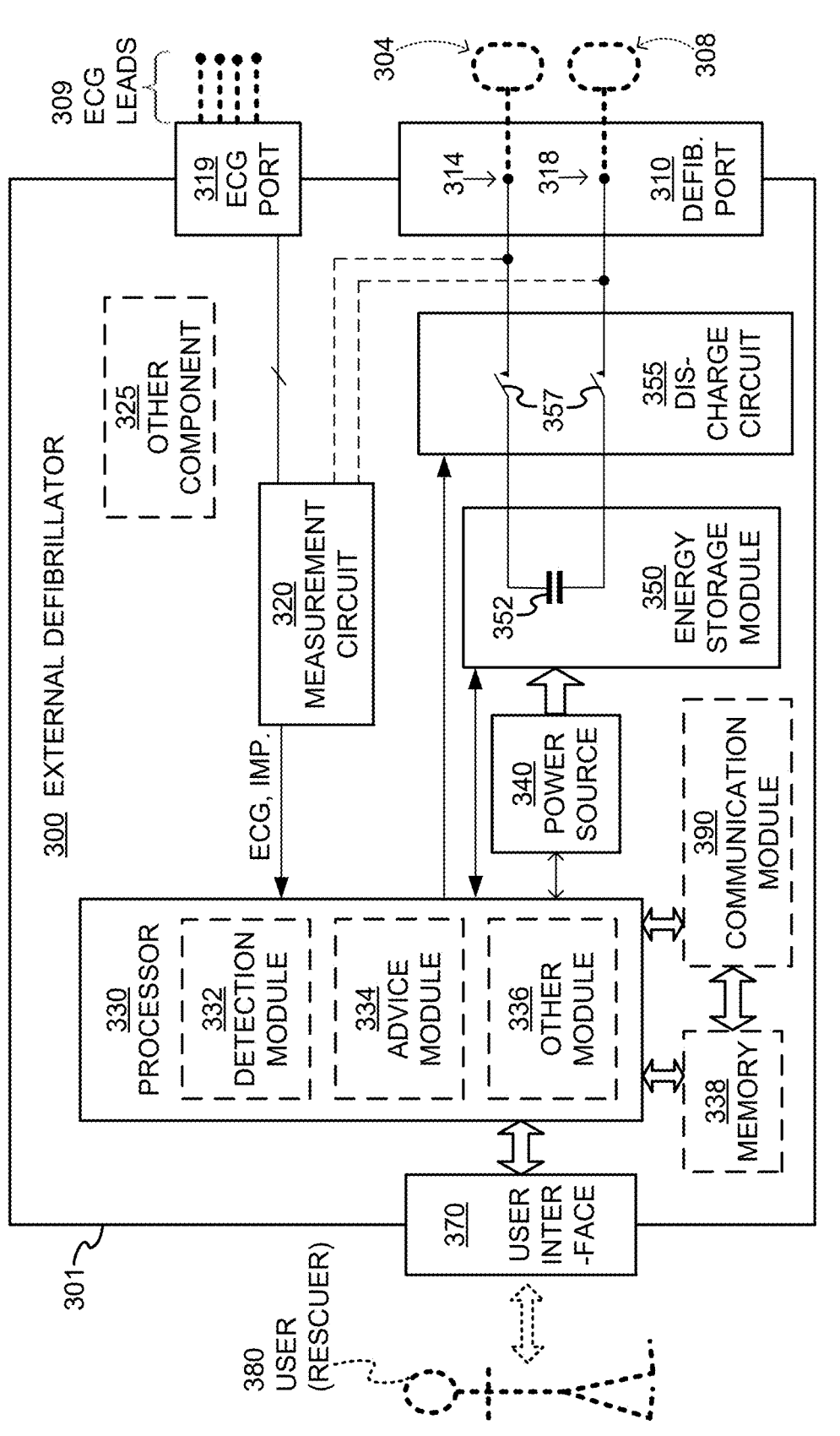
FIG. 3 is a functional block diagram showing components of an external defibrillator, such as the one shown in FIG. 1.

An example medical device can include a therapy module that is configured to output an energy delivery, such as a defibrillation shock. The medical device can also include sync mode circuitry that is coupled to the therapy module and configured to receive a generated artifact. The generated artifact can be indicative of a first energy delivery and the sync mode circuitry can generate an instruction for the therapy module to discharge a second energy delivery from the therapy module. In an example embodiment, the generated artifact can be substantially similar to a patient physiological parameter. In a further example embodiment, the generated artifact can be an electromagnetic artifact.

In another example, the electromagnetic artifact can be generated by the first energy delivery from another medical device and the electromagnetic artifact is included in the first energy delivery.

In a further example, a first electrode can be electrically connected to the therapy module by a first wire and a second electrode can be connected to another device by a second wire. The first and second wire can be at least partially intertwined such that the electromagnetic artifact is received by the first wire from the second wire. In another example embodiment, an electrocardiogram wire can be coupled to the sync mode circuitry and a second electrode can be connected to another device by a second wire. The electrocardiogram wire and the second wire can be at least partially intertwined such that the electromagnetic artifact is received by the electrocardiogram wire from the second wire.

In another example, a modifier can be included. The modifier can be configured to receive at least a portion of the first energy delivery and to generate the artifact in response to the first energy delivery. The generated artifact can be transmitted by the modifier and received by the sync mode circuitry. In an example embodiment, the modifier can be discrete from the medical device. In a further example embodiment, the modifier can be passive and configured to be energized by an induction power transfer from the first energy delivery, the energized modifier can output the generated artifact having one or more predetermined artifact characteristics. In another example embodiment, the modifier can be an active modifier and configured to be energized by an induction power transfer from the first energy delivery, the energized modifier can output the generated artifact having one or more artifact characteristics. In a further example, the one or more artifact characteristics can be selected from a plurality of artifact characteristics. Further, the plurality of artifact characteristics can be based on the first energy delivery.

An example dual sequential defibrillation system can include a first defibrillator and a second defibrillator. The first defibrillator can include a first therapy module that is configured to output a first energy delivery. The discharge of the first energy delivery can generate an artifact. The second defibrillator can include a second therapy module that is configured to output a second energy delivery, and sync mode circuitry that is coupled to the second therapy module. The sync mode circuitry can be configured to receive the generated artifact from the first therapy module and also configured to generate an instruction for the second therapy module to discharge the second energy delivery based at least in part on the received generated artifact from the first therapy module. In another example embodiment, the sync mode circuitry can include a delay module configured to determine a delay of one or more of the instruction or the output of the second energy delivery relative to the receiving the generated artifact. Example delays can include 100-150 milliseconds and 600 milliseconds.

In a further example embodiment, the sync mode circuitry can include an artifact sync mode that is configured to specifically detect the generated artifact and generate the instruction based on the detected artifact.

In another example embodiment, a first electrode can be connected to the first therapy module and a second electrode can be connected to the second therapy module and coupled to the sync mode circuitry. A first wire of the first electrode can be intertwined with a second wire of the second electrode and the generated artifact can be transmitted through the first wire of the first electrode and received by the second wire of the second electrode.

In a further example embodiment, a first electrode can be connected to the first therapy module via a first wire and an electrocardiogram lead can be connected to the second defibrillator and coupled to the sync mode circuitry. The first wire and the electrocardiogram lead can be at least partially intertwined such that the generated artifact is received by the electrocardiogram lead from the first wire during the discharge of the first energy delivery.

In another example embodiment, a modifier device can be included. The modifier device can be configured to generate the generated artifact and to transmit the generated artifact to the second defibrillator in response to the discharge of the first energy delivery.

In a further example embodiment, the sync mode circuitry can be further configured for the administration of a dual sequential defibrillation therapy.

In another example embodiment, the first defibrillator can include sync mode circuitry. The sync mode circuitry of the first defibrillator and the sync mode circuitry of the second defibrillator can be synced to one or more characteristics of an ECG signal. The sync mode circuities can also be configured to generate instructions such that the first energy delivery and the second energy delivery occur substantially simultaneously.

DETAILED DESCRIPTION

Described herein are methods and systems for controlling multiple defibrillation therapies, such as dual sequential defibrillation (DSD) and simultaneous defibrillation. DSD is the administration of multiple defibrillation therapies, or energy deliveries, the administration of each timed relative to one or more preceding administrations. Simultaneous defibrillation is the administration of multiple defibrillations, or energy deliveries, substantially concurrently. The administration of multiple defibrillations and/or energy therapies has been shown to assist with correcting an abnormal heart rhythm of a patient, including ventricular fibrillation, atrial fibrillation, and other rhythms considered shockable by a clinician. The systems and methods described below provide a controlled, adjustable and repeatable means for delivery of such defibrillation therapies so as to assist in the correction of an abnormal heart rhythm. FIGS. 1-3 explain a general overview of defibrillation therapy using a single defibrillator or therapy module for sake of simplifying the general explanation. FIGS. 4-10 relate specifically to DSD and/or simultaneous defibrillation using two or more therapy modules and/or defibrillators.

FIG. 1 is a diagram of a defibrillation scene in which a patient is receiving defibrillation therapy from a single external defibrillator 100. The person 82 is lying on his or her back and could be a patient in a hospital, or someone found unconscious, and then turned to be on their back. The person 82 is experiencing a cardiac arrhythmia in his or her heart 85, which could be Ventricular Fibrillation (VF) for example.

A portable external defibrillator 100 has been brought close to the person 82. At least two defibrillation electrodes 104, 108 are usually provided with an external defibrillator 100, and are sometimes called electrodes 104, 108. The electrodes 104, 108 are coupled with the external defibrillator 100 via respective electrode leads 105, 109. A rescuer (not shown) has attached electrodes 104, 108 to the skin of person 82 and actuates the defibrillator 100 to administer a brief, strong electric pulse 111 via electrodes 104, 108 through the body of person 82. Pulse 111, also known as a defibrillation shock, goes also through heart 85, in an attempt to remove the shockable arrhythmia (for example VF) and allowing the natural rhythm of the heart to resume, for saving the life of the person 82.

The defibrillator 100 can be one of different types, each with different sets of features and capabilities. The set of capabilities of the defibrillator 100 is determined by planning who would use it, and the training those rescuers would be likely to have. Examples are now described.

FIG. 2 is a table listing two main types of external defibrillators, and their primary users. A first type of defibrillator 100 is generally called a defibrillator-monitor because it is typically formed as a single defibrillation unit in combination with a patient monitor. A defibrillator-monitor is sometimes called monitor-defibrillator. A defibrillator-monitor is intended to be used by persons in the medical professions, such as doctors, nurses, paramedics, emergency medical technicians, etc. and often requires technical training on its operation. Such a defibrillator-monitor is intended to be used in a pre-hospital or hospital scenario.

As a defibrillator, the device can be one of different varieties, or even versatile enough to be able to switch among different modes that individually correspond to the device varieties. One variety is that of an automated defibrillator, which can determine whether a shock is needed and, if so, charge a therapy module of the device to a predetermined energy level and instruct and/or prompt the user to administer the shock. Some AEDs are also able to deliver the shock automatically to a person detected to be in a shockable rhythm, rather than wait for the user to press a button to deliver the shock. Another variety is that of a manual defibrillator where the user determines the need and controls administering the shock.

As a patient monitor, the device has features additional to what is minimally needed for mere operation as a defibrillator. These features can be for monitoring physiological indicators of a person in an emergency scenario. These physiological indicators are typically monitored as signals. For example, these signals can include a person's ECG (electrocardiogram) signal or impedance between two electrodes. Additionally, these signals can relate to the person's temperature, non-invasive blood pressure (NIBP), arterial oxygen saturation/pulse oximetry (SpO2), the concentration or partial pressure of carbon dioxide in the respiratory gases, known as capnography, and so on. These signals can be further stored and/or transmitted as patient data.

A second type of external defibrillator 100 is generally called an AED, which stands for "Automated External Defibrillator". An AED typically automatically makes the shock/no shock determination on whether to deliver defibrillation therapy to the patient. Indeed, it can sense enough physiological conditions of the person 82 via only the shown defibrillation electrodes 104, 108 of FIG. 1. In its present embodiments, an AED can either administer the shock automatically, or instruct the user to do so, e.g. by pushing a button. Being of a much simpler construction, an AED typically costs much less than a defibrillator-monitor. As such, hospitals, for example, may deploy AEDs at its various floors, in case the more expensive defibrillator-monitor is more critically being deployed at an Intensive Care Unit or other emergency situation of greater or prior need, and so on.

AEDs, however, can also be used by people who are not in the medical profession. More particularly, an AED can be used by many professional first responders, such as the police, firefighters, emergency medical personnel, etc. AEDs are often found in public locations especially those locations that tend to host large numbers of people. Such AEDs are often operated by rescuers with first-aid training or by a good Samaritan who has no training on the device at all. AEDs increasingly can supply instructions to whoever is using them and anticipate this wide variety of skill levels of its users.

AEDs are thus particularly useful because clinical response time is very critical when responding to someone suffering VF. Indeed, the people who are able to first reach the VF sufferer may not be and are often not in the medical professions.

There are additional types of external defibrillators that are not listed in FIG. 2. For example, a hybrid defibrillator can have aspects of an AED and also of a defibrillator-monitor. A usual such aspect is additional ECG monitoring capability among others.

FIG. 3 is a diagram showing components of an external defibrillator 300 made according to embodiments. These components can be, for example, in the external defibrillator 100 of FIG. 1. Additionally, the components of FIG. 3 can be provided in a housing 301, which can also be known as a casing 301. The external defibrillator 300 is intended for use by a user 380, who is the rescuer. The defibrillator 300 typically includes a defibrillation port 310, such as a socket in the housing 301. The defibrillation port 310 includes nodes 314, 318. The defibrillation electrodes 304, 308, which can be similar to the electrodes 104, 108, can be connected to the defibrillation port 310 so as to make an electrical connection with the nodes 314, 318, respectively. It is also possible that electrodes can be connected continuously to the defibrillation port 310, etc. Either way, the defibrillation port 310 can be used for guiding an electrical charge that has been stored in the defibrillator 300 to the person 82 through the electrodes.

If the defibrillator 300 is a defibrillator-monitor, as was described with reference to an example discussed in FIG. 2, then it will typically also have an ECG port 319 in housing 301, for plugging in ECG leads 309. ECG leads 309 can help sense an ECG signal, e.g. a 12-lead signal, or from a different number of leads. Moreover, a defibrillator-monitor could have additional ports (not shown), and another component 325 structured to filter the ECG signal, e.g., apply at least one filter to the signal so as to remove chest compression artifacts resulting from chest compressions being delivered to the person 82. The defibrillator 300 shown in FIG. 3 also includes a measurement circuit 320 that receives patient physiological signal(s) from the ECG port 319, and also from other ports, if provided. These physiological signals are sensed, and information about them is rendered by the circuit 320 as data, or other signals, etc.

If the defibrillator 300 is an AED, it may lack an ECG port 319. The measurement circuit 320 can obtain physiological signals through nodes 314, 318 instead, when defibrillation electrodes 304, 308 are attached to person 82. In these examples, a patient's ECG signal can be sensed as a voltage difference between the electrodes 304, 308. Further, impedance values sensed between the electrodes 304, 308 can detect, among other things, whether these electrodes 304, 308 have been inadvertently disconnected from the person.

The defibrillator 300 also includes a processor 330 that may be implemented in any number of ways. Such ways include, by way of example and not limitation, digital and/or analog processors such as microprocessors and digital-signal processors (DSPs); controllers such as microcontrollers; software running in a machine; programmable circuits such as Field Programmable Gate Arrays (FPGAs), Field-Programmable Analog Arrays (FPAAs), Programmable Logic Devices (PLDs), Application Specific Integrated Circuits (ASICs), any combination of one or more of these, and so on.

The processor 330 can include a number of modules. One such module is a detection module 332, which senses outputs of measurement circuit 320. Detection module 332 can include a VF detector. Thus, the person's sensed ECG can be used to determine whether the person is experiencing VF. Another such module in the processor 330 is an advice module 334, which arrives at advice based on output(s) of the detection module 332. Advice module 334 can include a Shock Advisory Algorithm, implement decision rules, and so on. The advice can be to shock, to not shock, to administer other forms of therapy, and so on. If the advice is to shock, some external defibrillator embodiments merely report the shock recommendation to the user, and prompt them to do it. Other embodiments further execute the advice, by administering the shock. If the advice is to administer CPR, the defibrillator 300 may further issue prompts for it, and so on. The processor 330 can include additional modules, such as the module 336, for other functions. In addition, if another component 325 is indeed provided, it may be operated in part by the processor 330, etc.

Defibrillator 300 optionally further includes a memory 338, which can work together with the processor 330. The memory 338 may be implemented in any number of ways. Such ways include, by way of example and not of limitation, nonvolatile memories (NVM), read-only memories (ROM), random access memories (RAM), any combination of these, and so on. The memory 338, if provided, can include programs for the processor 330, and so on. The programs can be operational for the inherent needs of the processor 330, and can also include protocols and ways that decisions can be made by the advice module 334. In addition, the memory 338 can store prompts for the user 380 and patient data, as needed.

The defibrillator 300 may also include a power source 340. To enable portability of the defibrillator 300, the power source 340 typically includes a battery. Such a battery can be implemented as a battery pack, which may be rechargeable or not. Sometimes, a combination is used, of rechargeable and non-rechargeable battery packs. Other embodiments of power source 340 can include AC power override that allows a rescuer to use AC power when such a source exists, but rely on the battery power if AC power is unavailable. In some embodiments, the power source 340 is controlled by the processor 330. The defibrillator 300 additionally includes an energy storage module 350. The module 350 is where some electrical energy is stored, when preparing the device for sudden discharge to administer defibrillation shock therapy to the patient. The module 350 can be charged from the power source 340 to the desired amount of energy, as controlled by the processor 330. In typical implementations, the module 350 includes one or more capacitors 352 that charge and help store the energy for later discharge, and so on.

The defibrillator 300 can also include a discharge circuit 355. The discharge circuit 355 can be controlled to permit the energy stored in the module 350 for discharge to the nodes 314, 318, and thus also to the defibrillation electrodes 304, 308. The discharge circuit 355 can include one or more switches 357. Those switches can be made in a number of ways, such as by an H-bridge, and so on, or other desirable configurations.

The defibrillator 300 further includes a user interface 370 for the user 380. For example, the interface 370 may include a screen to display what is detected and measured, provide visual feedback to the rescuer for their resuscitation attempts, and so on. The interface 370 may also include a speaker to issue voice prompts or otherwise audibly interact with the user and may additionally include various controls, such as pushbuttons, keyboards, and so on, as needed or desired. In addition, the discharge circuit 355 can be controlled by the processor 330, or directly by the user 380 through the user interface 370.

The defibrillator 300 can optionally include other components. For example, a communication module 390 may be provided for communicating with other machines. Such communication can be performed wirelessly, or via wire, or by infrared communication, and so on. This way, data can be communicated, such as patient data, incident information, therapy attempted, CPR performance, and the like. Another feature of a defibrillator can be CPR-prompting in which prompts are issued to the user, visual or by sound or otherwise, so that the user can administer CPR and/or receive feedback/instructions regarding the administration of CPR and/or delivery of shock therapy to the patient.

To synchronize, or otherwise coordinate timing of, multiple defibrillators to deliver simultaneous and/or sequential defibrillation, an artifact generated by one defibrillator during an energy delivery can be used to cause another defibrillator, similarly attached to the patient, to also administer an energy delivery to the same patient. The artifact, as described herein, can be an electromagnetic electrocardiogram (ECG) artifact that is generated by, or caused to be generated by, the energy delivery of one, or an initial, defibrillation by a defibrillator. The defibrillators can be inductively coupled, such as by intertwining various leads or wires of a second defibrillator with an electrode wire of the first defibrillator, and/or through the use of a modifier that is inductively coupled to both defibrillators. The other defibrillator(s) attached to the patient can be operated in a synchronized cardioversion mode (sync mode) that is capable of detecting the ECG artifact that is received via the inductive coupling of the other defibrillator(s) with the defibrillator administering an energy delivery. Various current defibrillators, defibrillator/monitors and/or AEDs already include a sync mode capable of administering an energy delivery in response to one or more characteristics of a patient's ECG. The generated artifact can substantially mimic one of the one or more characteristics that the defibrillation device is monitoring for a sync mode and/or the artifact can have one or more ECG characteristics that cause the sync mode of the defibrillation device to administer an energy delivery.

FIG. 4 shows an example system 400 for delivering multiple defibrillation therapies. The system 400 includes a pair of defibrillators 410 and 420 that include therapy modules 412, 422 that output an energy delivery to a patient through the electrode pairs 452, 454 and 462, 464. In the example shown, a first defibrillator 410 includes a therapy module 412 that is connected to electrode 452 by a wire 432 and to electrode 454 by wire 434. Energy delivery by the therapy module 412 through the electrodes 452, 454 can be manually or automatically initiated, or triggered. A second defibrillator 420 includes a therapy module 422 that is connected to electrode 462 by a wire 442 and to electrode 464 by wire 444. Additionally, the second defibrillator 420 includes a sync mode circuitry 424 that is connected to the therapy module 422. The sync module 424 can receive patient physiological data, such as from the electrodes 462, 464, and/or other patient physiological sensors, monitoring sources, equipment and/or other data sources. The sync mode circuitry 424 can monitor certain patient physiological parameters and/or generate an instruction and/or output to cause the therapy module 422 to discharge an energy delivery. In the system 400, the discharge of an energy delivery by the first defibrillator generates an artifact, such as an electromagnetic signal, that can be received, or detected, by the sync mode circuitry 424 of the second defibrillator 420. The second defibrillator 420 can receive the generated artifact through the electrodes 462, 464 connected thereto. In response to receiving the artifact, the sync mode circuitry 424 can generate the instructions to cause the therapy module 422 to also discharge an energy delivery.

In the example system 400 shown in FIG. 4, the artifact can be generated by and/or transmitted through the intertwining of one of the electrode wires, such as 434, of the first defibrillator 410 with one of the electrode wires, such as 444, of the second defibrillator 420. The intertwined portion 470 of the electrode wires 434, 444 are inductively coupled and/or can act as a rudimentary transformer. In this manner, an energy delivery discharged by the therapy module 412 of the first defibrillator 412 can induce a current in the electrode wire 444 of the second defibrillator. This induced current is, at least in part, the generated artifact in this example embodiment and can be received by one or more of the therapy module 422 and the sync mode circuitry 424 of the second defibrillator 420. In response to receiving and/or detecting the generated artifact, the sync mode circuitry 424 can output an instruction to the therapy module 422 to discharge, or output, an energy delivery.

The electrodes 452, 454, connected to the first defibrillator 410, and the electrodes 462, 464, connected to the second defibrillator 420, can be arranged such that one of the electrode pairs, 452, 454 or 462, 464 are located anterior-posterior (AP) on the patient and the other is located anterior-lateral (AL). In the AP arrangement, one pair of the electrodes is placed so that one electrode of the pair is located anterior the patient's heart and the other electrode of the pair is located posterior the patient's heart. Similarly, in the AL arrangement, one pair of electrodes is placed so that one electrode of the pair is located anterior the patient's heart and the other electrode of the pair is located lateral the patient's heart. For example, in the AP/AL arrangement, one pair of electrodes 452, 454 are arranged in the AP configuration and the other pair of electrodes, 462, 464, are arranged in the AL configuration. The intertwined wires of each of the defibrillators 410, 420 can be such that the wire 434 is connected to an AP electrode 454 and the wire 444 is connected to an AL electrode 464, i.e. AP/AL inductive coupling. Alternative inductive couplings can include AL/AP, AL/AL and/or AP/AP, in which one wire of one electrode pair of the first arrangement, AL or AP, is intertwined with one wire of the other electrode pair of the second arrangement, AL or AP. Other DSD and/or simultaneous defibrillation appropriate inductive couplings between the two defibrillators 410, 420 are possible such that the generated artifact can be generated/caused by one defibrillator 410 and received by the other defibrillator 420.

The generated artifact can be an induced electromagnetic artifact having artifact characteristic, such as a current, electromagnetic signal properties and/or other electromagnetic characteristics. For example, the induced current can have a magnitude that exceeds a threshold, such as a preset threshold, that causes the sync mode circuitry 424 to output an instruction to the therapy module 422. In another example, the generated artifact can be an electromagnetic signal that has one or more signal properties that cause the sync mode circuitry 424 to output the instruction to the therapy module 422. In a further example, the generated artifact can substantially mimic a patient physiological characteristic, such as a QRS complex or other physiological parameter that causes the sync mode circuitry 424 to generate the instructions. By substantially mimicking a patient physiological parameter that causes a sync mode of a defibrillator to output an energy delivery, the DSD and/or simultaneous defibrillation can be effected using one or more systems that generate an artifact with a defibrillator having a suitable sync mode and/or sync mode circuitry.

The sync mode circuitry 424 can also include a delay in the generated instructions. The delay can cause the therapy module 422 and/or the sync mode circuitry to delay a set period of time before triggering, or outputting, the energy delivery from the therapy module 422. The delay duration can be set by a user or automatically by the defibrillator 420 and/or the sync mode circuitry 424. The delay can be selected from one or more predetermined delays or can be a custom set delay that can also be based on physiological data of a patient, to which the defibrillator 420 and/or other physiological sensors and/or monitors are attached. The various physiological data can be sensed and/or received by the defibrillator 420, the sync mode circuitry 424 and/or other components and/or systems for use in determining a delay to include in the generated instructions. In example embodiments, the delay can be between 0.1 and 20 milliseconds and/or between 100 and 150 milliseconds. The length of the delay can be based on clinical testing that indicates a preferred delay duration for administering the second energy delivery subsequent to a prior energy delivery.

Alternatively, the sync mode circuitry 424 can be coupled to a timing control unit and/or another module, circuit, mode or other timing source/control, to calculate, implement and/ or time the delay. As described above, the calculated delay can be included in the instructions that the therapy module 422 receives. Alternatively, the timing control unit can delay the reception and/or transmission of the instructions by/to the therapy module 422. In a further example, the timing control unit can be integrated with one or more of the sync mode circuitry 424 and/or the therapy module 422.

The wires 434, 444 of the electrodes 454 and 464 can be manually intertwined by a user or can come pre-intertwined for use in DSD and/or simultaneous defibrillation therapies. In the embodiment in which a user manually intertwines the wires 434 and 444, one or more of the defibrillators 410, 420 can provide instructions regarding the intertwining, such as a procedure for intertwining the wires 434 and 444, the number of times the wires 434 and 444 are intertwined and/or other characteristics of the intertwined portion 470 required and/or desired for administration of a DSD and/or simultaneous defibrillation therapy. Alternatively, one or more devices and/or systems can be used to assist with the proper intertwining of the electrode wire for use with the administration of a DSD and/or simultaneous/near simultaneous defibrillation therapy.

FIG. 5 illustrates another example system 500 for administering multi-defibrillation therapies. The system 500 includes defibrillators 510 and 520 that output energy deliveries to a patient. The first defibrillator 510 can include a therapy module 512 that can output an energy delivery to a patient through electrodes 552, 554 that are coupled to the therapy module 512 via wires 532, 534. The second defibrillator 520 can include sync mode circuitry 524 coupled to a therapy module 522 that can output an energy delivery to a patient through electrodes 562, 564 that are coupled to the therapy module 522 via wires 542, 544. Similar to the system 400 of FIG. 4, the sync mode circuitry 524 of the second defibrillator 522 can generate instructions to cause the therapy module 522 to output an energy delivery in response to receiving and/or detecting an artifact caused by an output of an energy delivery by the therapy module 512 of the first defibrillator 510.

In the example system 500 of FIG. 5, the second defibrillator 510 also includes electrocardiogram (ECG) electrodes 582, 584 coupled, via ECG leads 581, 583, to the sync mode circuitry 524. The ECG electrodes 582, 584 can gather patient physiological data that the defibrillator 520, or subcomponents/subsystems thereof, can analyze and/or use for various defibrillator functions, including outputting the physiological data for a user. The sync mode circuitry 524 can monitor the patient physiological data acquired via ECG electrodes 582, 583 to cause the sync mode circuitry 524 to output an instruction to the therapy module 522 to output an energy delivery. In an example embodiment, the ECG data can include a patient's heart rhythm and the sync mode circuitry 524 can output the instruction in response to an abnormal heart rhythm or detection of a QRS complex.

In the example system 500, the wire 534 of the first defibrillator 510 can be intertwined with the ECG lead 583, along an intertwined portion 572, to cause the artifact to be generated and/or transmitted by an energy delivery from the therapy module 512 of the first defibrillator 510. The generated artifact can be transmitted to the sync mode circuitry 524 of the second defibrillator 520 via the ECG lead 583. The received generated artifact can cause the sync mode circuitry 524 to generate an instruction to the therapy module 522 to output an energy delivery. Similarly, to the system 400 of FIG. 4, the energy delivery by the therapy module 522 can include a delay to space the energy delivery relative to the energy delivery of the therapy module 512 of the first defibrillator 510.

Similar to the example system of FIG. 4, the placement of the electrodes 552, 554, 562, 564 and the ECG electrodes 582, 584 can have an effect on the inductive coupling of the defibrillators 510, 520. In the example system 500, one of the ECG electrodes 582, 584 can be a right arm (RA) electrode and the other ECG electrode can be a right leg electrode. The intertwining of the wire 534 and a RA or RL electrode is done to assist with preventing the second defibrillator 520 from administering an inadvertent energy delivery that is an energy delivery not triggered by the artifact caused by the first defibrillator 510. The inadvertent energy delivery can happen if an ECG signal of a patient, as detected via one or more ECG electrodes 582, 584, would otherwise cause a sync mode, or sync mode circuitry 524, of the second defibrillator 520 to inadvertently trigger the second defibrillator 520 to administer an energy delivery. In an example embodiment in which the ECG electrodes 582, 584 are affixed to a patient, the placement of the RA and RL electrodes can be reversed to prevent inadvertent triggering of an energy delivery. For example, if the wire 534 is intertwined with RA ECG electrode 582, then the RA ECG electrode 582 should then be placed where the RL ECG electrode 584 would otherwise go and the RL ECG electrode 584 should be placed where the RA ECG electrode 582 would have been placed. In a further example embodiment, the ECG electrodes 582, 584 may not be placed on a patient and instead both are connected to a conductive medium, such as a wire or resistor. To effect proper DSD and/or simultaneous defibrillation, the ECG lead intertwined with the wire 534 needs to be the ECG lead from which synchronization can be performed using the sync mode, or sync mode circuitry 524, of the defibrillator 520. Alternatively, other ECG leads can be inductively coupled with a wire of an electrode to effect the proper synchronization for administration of a DSD and/or simultaneous defibrillation.

FIG. 6 illustrates yet another example system 600 for administering multiple defibrillation therapies, such as DSD and/or simultaneous defibrillation. The example system 600 includes defibrillators 610, 620 that can output one or more energy deliveries to a patient to which the defibrillators 610, 620 are attached. A first defibrillator 610 can include a therapy module 612 that is coupled to an optional artifact generator 616. The therapy module 612 can be coupled to electrodes 652, 654 via wires 632, 634 to output an energy delivery to a patient. A second defibrillator 620 can include a therapy module 622 and sync mode circuitry 624 that includes an optional delay 625. The therapy module 622 can be coupled to electrodes 662, 664 via wires 642, 644 to output an energy delivery to a patient. An energy discharge by the therapy module 612 of the first defibrillator 610 can cause an artifact to be generated and/or transmitted to the sync mode circuitry 624 of the second defibrillator 620 to cause the sync mode circuitry 624 to generate instructions to cause the therapy module 622 to output an energy delivery, similar to the above described systems.

A modifier 670 can be inductively coupled between the wire 634 and wire 644 to generate and/or transmit an artifact. The modifier 670 can be a separate element that can be attached or inductively coupled to the wires 634 and 644 and as such, could be retrofit to existing defibrillators. In an example embodiment, the wires 634 and 644 can be wrapped about one or more portions of the modifier 670 to induce and/or receive a current and/or artifact transmitted through or form the modifier 670. Alternatively, one or more of the wires 634, 644 can include the modifier 670. Further, the modifier 670, while shown in FIG. 6, can be used with other DSD and/or simultaneous defibrillation therapy systems, such as those shown in FIGS. 4 and 5, to assist with the inductive coupling necessary to transmit and/or generate the artifact.

The first defibrillator 610 can include the optional artifact generator 616 coupled to the therapy module 612. The artifact generator 616 can generate an electromagnetic artifact that can be included in the energy delivery output of the therapy module 612. The electromagnetic artifact can include one or more electromagnetic characteristics that can cause the sync mode circuitry 624, therapy module 622 and/or second defibrillator 620 to cause the output of an energy delivery by the therapy module 622 of the second defibrillator 620. The artifact generated by the artifact generator 616, and subsequently discharged with the energy delivery by the therapy module 612, can be passed directly through, or modified by, the modifier 670 to transmit the generated artifact to the wire 644.

The modifier 670 can include the ability to wave shape the artifact, such as a signal, that is transmitted through or generated by the modifier 670. Waveshaping the artifact can include widening the artifact duration, modifying the amplitude of the artifact, and/or delaying the transmission of the artifact. Waveshaping can assist the administration of DSD and/or simultaneous defibrillation as the artifact generated by the first defibrillator 610 may not be ideally shaped, ideally delayed, or have ideal characteristics, to cause the sync mode, or sync mode circuitry 624, of the second defibrillator 620 to administer an energy delivery in response to the artifact, in a desired manner. The modifier 670 can assist with forming and/or modifying the artifact to cause the second defibrillator 620 to administer an energy delivery as desired in response to the artifact.

The modifier 670 can be a passive or active modifier. In the passive form, the modifier 670 can include circuitry that is inductively coupled to the wire 634 to receive the artifact and transmit the artifact "as is" or modified to the wire 644. The passive circuitry of the modifier 670 can modify the artifact in a predetermined manner as determined by the passive circuitry. Example passive circuitry can filter the artifact such that the artifact has certain electromagnetic properties or can modify the artifact to alter one or more electromagnetic characteristics of the artifact in a known and/or predetermined manner as determined by the passive circuitry and its properties.

In the active form, the modifier 670 can include a powered circuit that generates and/or modifies the artifact and that can derive power from the inductively coupled wire 634. Alternatively, the modifier 670 can include a power source contained within, such as a battery, or can derive power from another source, such as an external power source connected to the modifier 670. Using the powered circuitry, the artifact output and/or transmitted by the modifier 670 can have consistent electromagnetic properties. These electromagnetic properties can be further selectable and/or modifiable. In this way, the artifact can act as a form of data transmission to cause the sync mode circuitry 624 to respond in a known and/or desired manner to receiving the artifact from the modifier 670.

The sync mode circuitry 624 can include a delay 625 that can calculate and/or implement a delay in the output of the energy delivery by the therapy module 622 of the second defibrillator 620. The delay can be included in the instructions generated by the sync mode circuitry 624, can delay the transmission/reception of the instructions and/or otherwise delay the output of the energy delivery. The delay can be calculated, such as based on one or more physiological parameters/characteristics of the patient, or can be predetermined, such as selected from one or more delays/delay durations. The delay 625 can be selected to assist with the efficacy of the sequential defibrillations, or energy deliveries, in a DSD therapy. The energy deliveries can require a minimum and/or maximum delay between the energy deliveries in order to have maximum effect in correcting the abnormal heart rhythm.

While the above described systems, such as those shown in FIGS. 4-6, are shown to include two defibrillators, the systems described systems can include additional defibrillators that are coupled together to, or otherwise, receive the generated artifact to cause the output of additional energy deliveries. Alternatively, the described systems can be implemented in a single device that can include multiple therapy modules to output the multiple defibrillation therapies.

Additionally, the sync mode circuitry, such as shown and described in the above examples, can be implemented in different forms and/or states. For example, the sync mode circuitry can be a stand-alone, or separate, module of/in the defibrillator(s) or can be included as part of the processor, such as instructions which are executed by the processor. Alternatively, the sync mode circuitry can be a sub-module of module switching circuitry for defibrillators and/or device that include such capabilities. Further, the various functions of the sync mode circuitry described can be implemented using one or more components and/or systems of a medical device, such as a defibrillator, defibrillator/monitor and/or an AED.

FIG. 7 is a diagram of an example passive modifier circuit 700. The modifier circuit 700 is a passive circuit that is inductively coupled to two defibrillators, such as shown in the system of FIG. 6. The modifier circuit 700 includes an input 710 that is inductively coupled to a first defibrillator. To inductively couple the defibrillator, the input 710 can include an inductor and/or the input 710 can be wrapped about an output of the defibrillator. The inductive coupling of the modifier circuit 700 and a defibrillator induces a current in the modifier circuit 700. The induced current then flows through a modifier section 720 that can modify the current flow through the modifier circuit 700. In the example shown, the modifier section 720 includes a diode bridge electrically connected in parallel with a capacitor. The current then passes to the output 730 of the modifier circuit 700. Much like the input 710, the output 730 is inductively coupled to a defibrillator. The defibrillator coupled to the output 730 is different and/or separate from the defibrillator coupled to the input 710. The output 730 transmits and/or generates the artifact that will be received by the inductively coupled defibrillator to cause an output of an energy delivery from the inductively coupled defibrillator.

FIG. 8 is a diagram of an example active modifier circuit 800. The active modifier circuit 800 includes an input 810 that is inductively coupled to a first defibrillator and an output 830 that is inductively coupled to a second defibrillator. An energy delivery by the first defibrillator can generate, or cause the modifier circuit 800 to generate, an artifact that is then transmitted through the inductive coupling, to the second defibrillator. An active modifier 820 section of the active modifier circuit 800 can modify and/or generate the artifact. The active modifier 820 can include resistors, capacitors, multivibrators and/or other circuit elements to modify and/or generate the artifact that is received by the second defibrillator. Power for the active modifier circuit 800 can be derived from the inductive coupling of the active modifier circuit 800 and the first defibrillator and/or the active modifier circuit 800 can include an internal, or external, power source 812, such as a battery.

Figure 9:
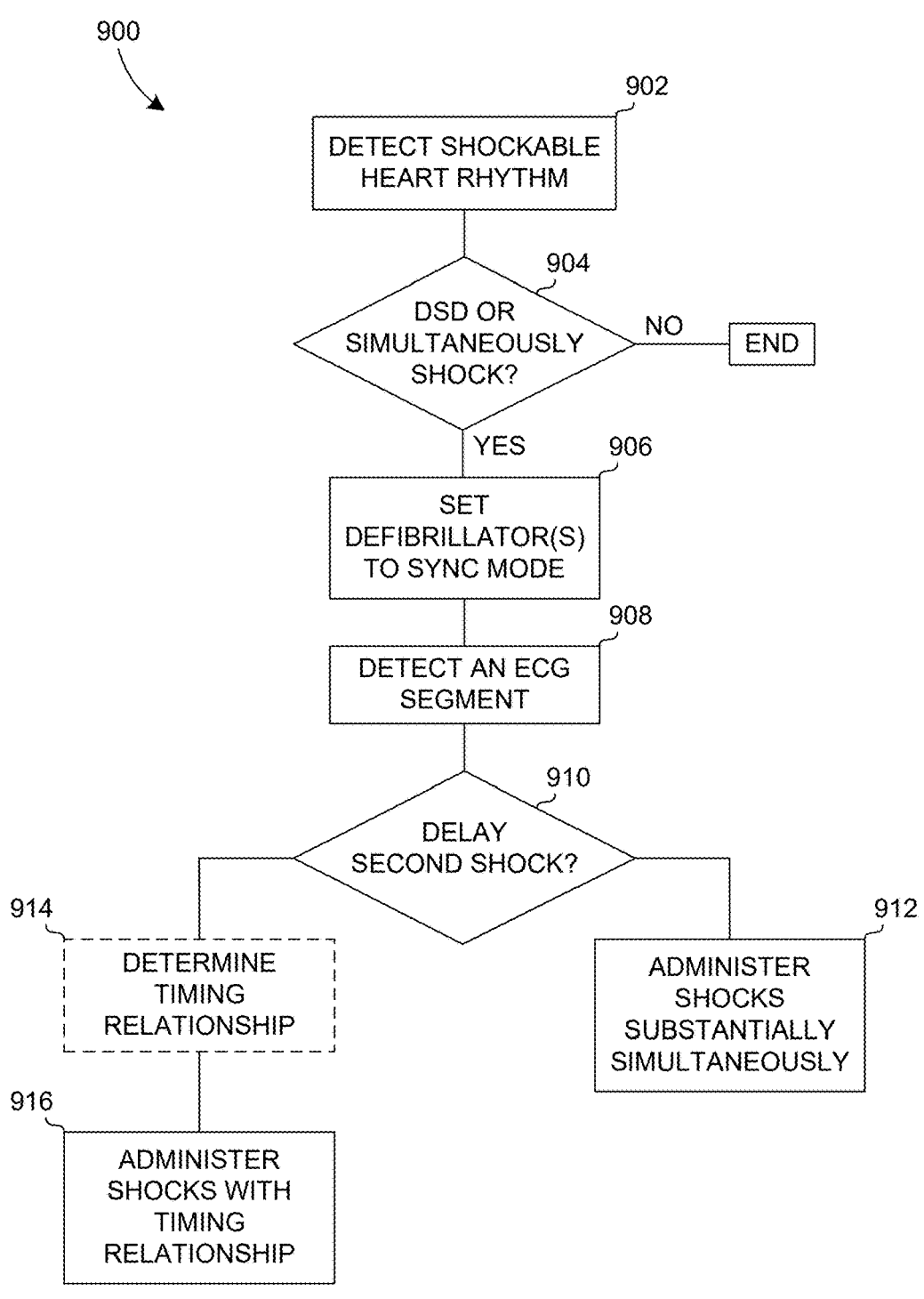
FIG. 9 is an example process for administering multiple defibrillation therapies.

FIG. 9 illustrates an example process 900 for administering multiple defibrillation therapies. The process 900 includes detecting a shockable heart rhythm at 902. A shockable heart rhythm can include a patient experiencing ventricular fibrillation (VF) or atrial fibrillation (AF), for example. The systems described above can be used to administer DSD and/or simultaneous defibrillation therapies to assist with correcting a heart rhythm of a patient, such as one experiencing VF or AF.

At 904, the decision to administer DSD or simultaneous shocks is made. If the decision is made to administer DSD and/or simultaneous shock therapy, one or more defibrillators connected to a patient are set to one or more sync modes at 906. In an example embodiment, one defibrillation, the defibrillator providing the initial shock, or energy delivery, is not required to be set to a sync mode as the discharge of the energy causes the other defibrillator(s), set in a sync mode, to administer a sequential defibrillation. In another example, the defibrillators can all be set to a sync mode such that the defibrillators can administer a sequential or simultaneous defibrillation therapy.

At 908, optionally, an ECG segment can be detected. The detected ECG segment can be a particular ECG segment that the process 900 is waiting and/or looking for. This detected ECG segment can be used in other elements of the process 900 and/or to time the various elements of the process 900.

At 910, a decision to delay the second shock is made. If no delay is desired and/or indicated, such as by the detected ECG segment, then the shocks from the defibrillators is delivery substantially simultaneously at 912.

If a delay is desired and/or required, then an optional timing relationship can be determined at 914. The timing relationship can be calculated and/or selected to include a delay for delivering the second, or subsequent, shock after the first, or prior, shock. The delay can space the shocks to assist with the effectiveness of the administration of the defibrillation therapy.

At 916, the sequential shocks are administered. If the optional timing relationship was determined at 914, then the sequential shocks are administered according to the timing relationship. If no timing relationship is determined and/or required, then the shocks proceed substantially sequentially, with a subsequent shock following the one administered prior shock. While no timing relationship may have been determined at 914, one or more of the defibrillators administering the subsequent shock can include hardware to cause a delay in the administration of the subsequent shock.

Figure 10:
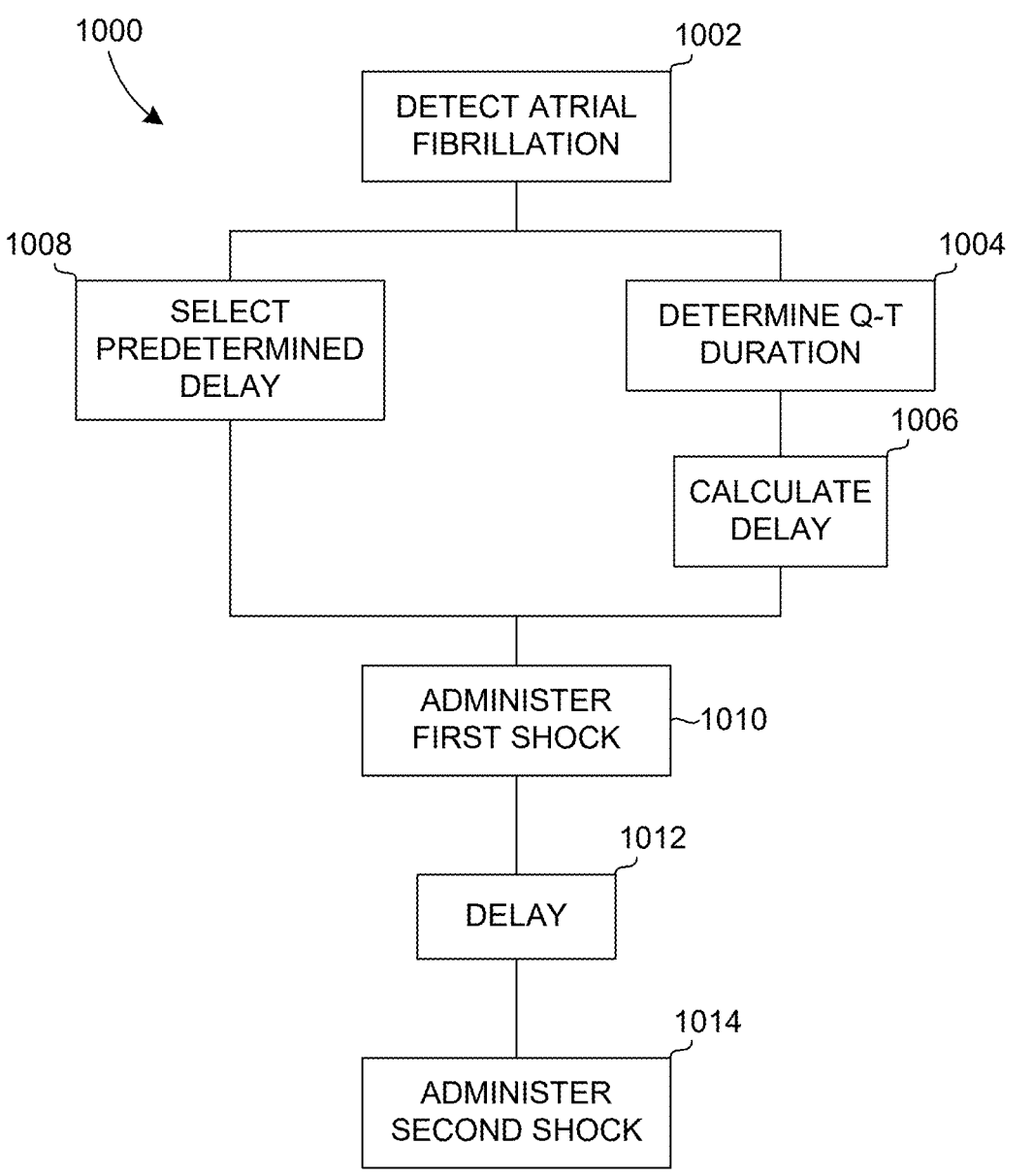
FIG. 10 is an example flow chart showing administration of multiple defibrillation therapies.

FIG. 10 is an example flow chart 1000 showing administration of multiple defibrillation therapies for use with a patient experiencing atrial fibrillation. At 1002, the atrial fibrillation of the patient is detected. To administer the DSD or simultaneous defibrillation therapy, two options can be used to set a delay, either a calculation of the delay or selection of a delay. The defibrillation device can include a specific DSD sync mode that can detect the artifact and introduce an appropriate delay for safe and effective DSD and/or simultaneous defibrillation therapy administration. The specific DSD sync mode can be implemented with hardware, software or a combination thereof. The DSD sync mode can include routines that assist with preventing the administration of the sequential energy delivery at an inappropriate time, such as during a T-wave of the patient.

In an example in which the delay is selected, a predetermined delay can be selected at 1008. The selected predetermined delay can be selected such that administration of the second shock is unlikely to occur during a T-wave of the patients ECG. Administration of a shock on the T-wave can cause the patient to go into ventricular fibrillation. To avoid this, the delay can be selected to increase the probability that the T-wave is avoided during administration of the second shock. In an example embodiment, the selected predetermined delay can be 600 milliseconds after the first shock. To sync the timing of each of the defibrillators, each of the defibrillators can be synced to an R-wave of the patient's ECG. This can then be used for simultaneous defibrillation or for timing the delay of the second shock relative to the administration of the first shock.

In an example in which the delay is calculated the patient's ECG can be analyzed to determine a Q-T duration of the patient at 1004. The delay can then be calculated at 1006 such that the administration of second shock avoids the T-wave of the patient's ECG. The calculated delay can be customized to the patient and their current physiological parameters.

At 1010, the first shock is administered and then a delay 1012 is waited and the second shock is administered at 1014 once the delay duration has expired.

In a further example, simultaneous defibrillation can be used to assist in correcting atrial fibrillation of the patient. In administering simultaneous defibrillation, no delay is required and the defibrillators are synced such that the shocks are administered substantially simultaneously. To sync the defibrillators, the patient's ECG can be analyzed and each of the defibrillators can be synced to administer shocks on an R-wave of the patient's ECG.

Figure 11:
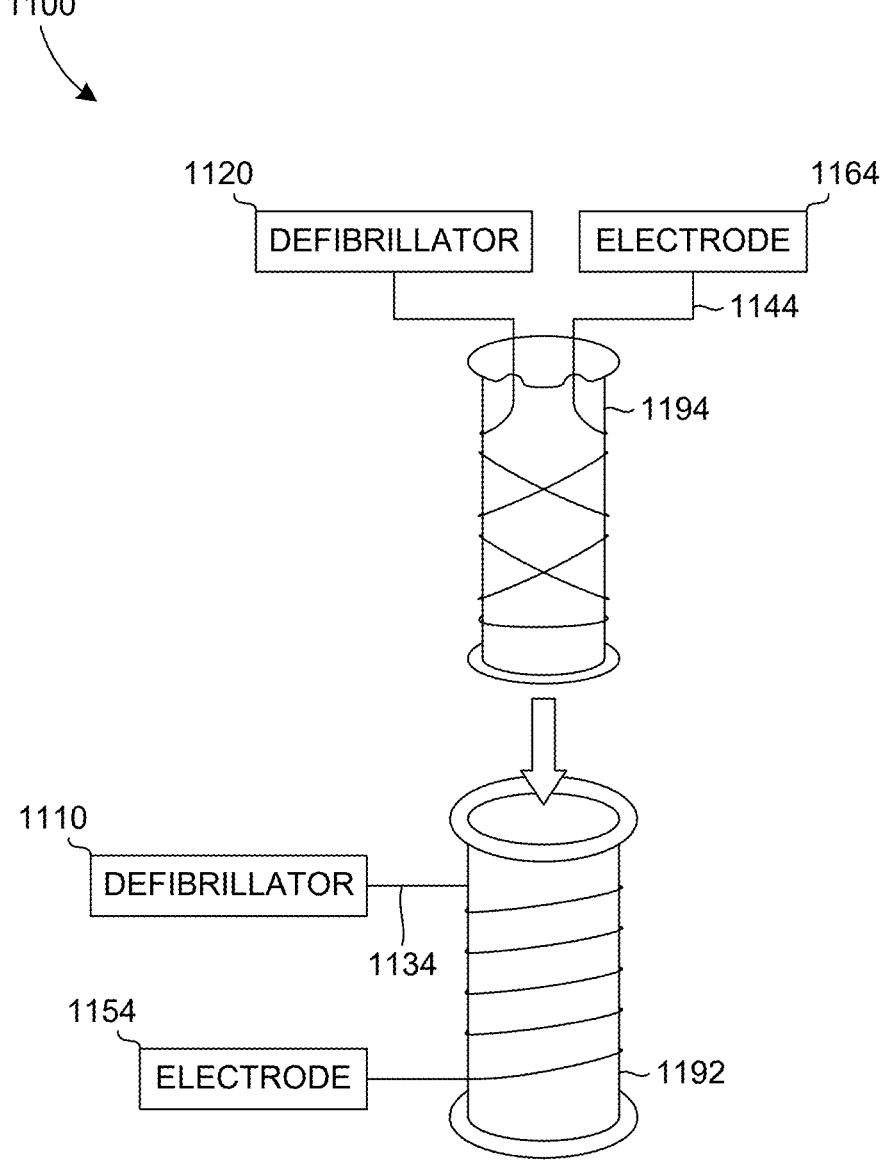
FIG. 11 shows example hardware for intertwining wires.

FIG. 11 illustrates an example system 1100 that includes a device that can be used to assist with intertwining wires for use with a DSD and/or simultaneous defibrillation system, such as those described above. The device includes a first part 1192 and a second part 1194, both of which are shown substantially cylindrically shaped. The first part 1192 has a wire 1134 wrapped one or more times about the first part 1192. One end of the wire 1134 is connected to a first defibrillator 1110 and the other end of the wire 1134 is connected to an electrode 1154. The electrode 1154 is an electrode of an electrode pair that is connected to the first defibrillator 1110. The second part 1194 has a wire 1134 wrapped one or more times about the second part 1194. One end of the wire 1144 is connected to a second defibrillator 1120 and the other end of the wire 1144 is connected to an electrode 1164. The electrode 1164 is an electrode of an electrode pair that is connected to the second defibrillator 1120. The second part 1194 can include one or more features, such as the notches shown, to allow the wire 1144 to be wrapped around and extend from the second part 1194 as necessary and/or desired. With the wires 1134 and 1144 wrapped about the first and second parts 1192, 1194, the second part 1194 can be inserted within the first part 1192, as indicated by the arrow. The insertion of the wire 1144 wrapped second part 1194 into the wire 1134 wrapped first part 1192 creates a transformer, or transformer-like device, that inductively couples the wires 1134 and 1134, allowing for the generation and/or transmission of a generated artifact from, or caused by, the first defibrillator 1110 to the second defibrillator 1120.

FIG. 12 illustrates another example system 1200 that includes a device that can be used to assist with intertwining wires for use with a DSD and/or simultaneous defibrillation system, such as those described above. The device includes a first part 1292 and a second part 1294, both of which are shown as substantially plate shaped. The first part 1292 and the second part 1294 are connected by a hinge 1296, allowing the first part 1292 and second part 1294 to be folded over each other, such that the first part 1292 and the second part 1294 are substantially adjacent. A wire 1234, connecting a first defibrillator 1210 to an electrode 1254, can be wrapped about the first part 1292. Similarly, a wire 1244, connecting a second defibrillator 1220 to an electrode 1264, can be wrapped about the second part 1294. As discussed above, each of the electrodes 1254, 1264, are one of a pair of electrodes that is connected to the first defibrillator 1210 and second defibrillator 1220, respectively. With the wires 1234, 1244 wrapped about the first and second parts 1292, 1294, the first part 1292 and second part 1294 can be folded, using the hinge 1296, to place the first part 1292 substantially along the second part 1294. Arranging the wire 1234 wrapped first part 1292 and the wire 1244 wrapped second part 1294 in such a manner forms a transformer, or transformer-like device, that inductively couples the wires 1234 and 1244, allowing for the generation and/or transmission of a generated artifact, or caused by, the first defibrillator 1210 to the second defibrillator 1220.

FIG. 13 illustrates an example system 1300 that includes a wire module 1302 for use with a DSD and/or simultaneous defibrillation system, such as those described previously. The wire module 1302 contains pre-intertwined wires and connections to connect the wire module 1302 to one or more defibrillators and/or electrodes. In the example shown, the wires module 1302 includes ports 1322 and 1324 to which electrodes can be attached and includes plugs 1312 and 1314 that can be connected to defibrillators. The plug 1312 can be electrically connected, through the wire module 1302, to the port 1322 and the plug 1314 can be electrically connected, via the wire module 1302, to the port 1324. A first defibrillator and a first electrode can be connected to the plug 1312 and port 1322, respectively, to couple the first electrode to the first defibrillator. Similarly, a second defibrillator and a second electrode can be connected to the plug 1314 and port 1324, respectively, to couple the second electrode to the second defibrillator. As discussed above, the first and second electrodes are an electrode of an electrode pair that are connected to the first and second defibrillators. The inductive coupling to generate and/or transmit a generated artifact from, or caused by, the first defibrillator to the second defibrillator is facilitated by the intertwined and/or otherwise connected wires, within the wire module 1302.

The above described systems and/or methods can be used to administer sequential and/or substantially simultaneous defibrillation therapies. The administration of such therapies can increase the effectiveness of defibrillation therapy administration in correcting one or more conditions of a patient's heart rhythm.

It will be appreciated that variants of the above-disclosed and other features and functions, or alternatives thereof, may be combined into many other different systems or applications. Other embodiments Various presently unforeseen or unanticipated alternatives, modifications, variations, or improvements therein may be subsequently made by those skilled in the art which are also intended to be encompassed by the following claims.

What is claimed is:

1. A modifier coupled to a first defibrillation device and to a second defibrillation device, wherein the modifier is configured to:

receive, from the first defibrillation device, a signal indicating an output of a first electrical shock by the first defibrillation device; and in response to receiving the signal, cause the second defibrillation device to output a second electrical shock.

2. The modifier of claim 1, wherein the modifier is inductively coupled to the first defibrillation device and is inductively coupled to the second defibrillation device.

3. The modifier of claim 1, wherein the modifier comprises a diode bridge electrically connected, in parallel, with a capacitor.

4. The modifier of claim 3, wherein the diode bridge and the capacitor are connected, in parallel, with the first defibrillation device and the second defibrillation device.

5. The modifier of claim 1, wherein the modifier comprises an active circuit that is powered by a power source.

6. The modifier of claim 1, wherein the modifier is inductively coupled to the second defibrillation device.

7. A system, comprising:

a first conductor connecting a first defibrillator to a first electrode;

a second conductor connecting a second defibrillator to a second electrode; and a device comprising a first part and a second part, the first conductor being wrapped around the first part, the second conductor being wrapped around the second part and being inductively coupled to the first conductor.

8. The system of claim 7, wherein the first part is cylindrical and has a first radius, wherein the second part is cylindrical and has a second radius, the second part at least partially enclosing a space, the second radius being longer than the first radius, and wherein the first part is disposed in the space.

9. The system of claim 8, further comprising a notch in a rim of the first part, wherein the first conductor is partially disposed in the notch.

10. The system of claim 7, wherein the device further comprises a hinge connecting the first part and the second part.

11. The system of claim 10, wherein the first part and the second part are folded over each other by the hinge.

12. The system of claim 7, wherein a first electrical shock is output by the first defibrillator via the first conductor and a second electrical shock is output by the second defibrillator via the second conductor.

13. The system of claim 12, wherein the first electrical shock output via the first conductor generates an artifact in the second conductor, and wherein the artifact causes the second defibrillator to output the second electrical shock.

14. A device configured to inductively couple a first connector and a second connector, the first connector being connected to a first defibrillator, the second connector being connected to a second defibrillator.

15. The device of claim 14, comprising:

a first part configured to be wrapped with the first connector; and a second part configured to be wrapped with the second connector.

16. The device of claim 15, wherein the first part is cylindrical and has a first radius, wherein the second part is cylindrical and has a second radius, the second part at least partially enclosing a space, the second radius being longer than the first radius, and wherein the first part is disposed in the space.

17. The device of claim 16, further comprising a notch in a rim of the first part, wherein a first conductor is partially disposed in the notch.

18. The device of claim 15, wherein the device further comprises a hinge connecting the first part and the second part.

19. The device of claim 14, further configured to:

couple a first connector to a third connector, the third connector being connected to a first electrode; and couple a second connector to a fourth connector, the fourth connector being connected to a second electrode.

* * * * *